(12) United States Patent
Lee et al.

(10) Patent No.: US 9,150,477 B1
(45) Date of Patent: Oct. 6, 2015

(54) SYSTEM FOR REMOVING SALT FROM A RICH MONO ETHYLENE GLYCOL STREAM

(71) Applicant: Cameron Solutions Inc., Houston, TX (US)

(72) Inventors: Joseph Min-Hsiun Lee, Houston, TX (US); Gary W. Sams, Spring, TX (US)

(73) Assignee: Cameron Solutions, Inc., Houston, TX (US)

( * ) Notice: Subject to any disclaimer, the term of this patent is extended or adjusted under 35 U.S.C. 154(b) by 0 days.

(21) Appl. No.: 14/307,217

(22) Filed: Jun. 17, 2014

(51) Int. Cl.
*C07C 29/76* (2006.01)
*B01D 3/06* (2006.01)

(52) U.S. Cl.
CPC .. *C07C 29/76* (2013.01); *B01D 3/06* (2013.01)

(58) Field of Classification Search
CPC .................................. C07C 29/76; B01D 3/06
See application file for complete search history.

(56) References Cited

U.S. PATENT DOCUMENTS

2003/0118989 A1* 6/2003 Rosenow et al. ................. 435/6

* cited by examiner

*Primary Examiner* — Yong Chu
(74) *Attorney, Agent, or Firm* — Gable Gotwals

(57) ABSTRACT

A system for, and method of, recovering salt from a rich mono ethylene glycol MEG stream includes a flash separator having a desanding hydrocyclone located in the hot MEG recycle loop of the flash separator; a first solids fluidization device located at the bottom end of the flash separator's brine column; a second desanding hydrocyclone arranged to receive a salt slurry stream created by the first solids fluidization device; and an accumulator located downstream of the second desanding hydrocyclone and having a second solids fluidization device located at its bottom end. Each solids fluidization device includes means for causing the motive fluid to exit the device in a swirling motion to fluidize the salt components contained in the resident fluid. The overflow from the second desanding hydrocyclone is the motive fluid for the brine column and a produced water, condensate water, or seawater stream is the motive fluid for the accumulator.

15 Claims, 3 Drawing Sheets

SYSTEM FOR REMOVING SALT FROM A RICH MONO ETHYLENE GLYCOL STREAM

BACKGROUND OF THE INVENTION

This invention relates to processes designed to treat mono ethylene glycol (MEG) used in the oil and gas industry, especially in offshore locations, to control hydrates formation. More particularly, the invention relates to MEG reclamation processes which are designed to remove salts and other contaminants from a wet MEG feed stream.

In the oil and gas industry, dry (lean) MEG is used to control the formation of hydrates within the produced stream. The now wet (rich) MEG is, in turn, dried by way of a MEG reclamation process so the MEG can be used again in hydrate control.

The unit used to recover MEG usually includes three sections: pre-treatment, flash separation, and MEG regeneration. Those sections can be followed by salt management and calcium removal sections.

In the pre-treatment stage, the rich MEG containing some dissolved gas and hydrocarbon liquids must pass through a three-phase separator vessel. The gas is flashed and recovered hydrocarbon liquids are sent to the production separator. The rich MEG is sent to a flash separator. The rich MEG stream comprised of produced water and MEG is fed to the flash separator where it is brought into contact with a hot recycle stream of MEG. The flash separator operates under vacuum. The MEG and water components of the rich MEG stream are flashed and exit through the top of the flash separator where they are sent to the MEG distillation column for regeneration. The salt components of the rich MEG stream precipitate in the flash separator.

The MEG regeneration section is a refluxed distillation column. The distillation column also operates under vacuum and distills the water from the MEG-water vapors coming off the top of the flash separator. Salt-free, lean MEG produced at the bottom of the distillation column is pumped to storage for reuse. The vaporized water passes overhead from the distillation column. The water is condensed and collected in the reflux drum. A small amount is returned to the distillation column as reflux, and the remaining is routed to treatment.

The salt crystals that precipitate in the flash separator are separated by gravity to the bottom of the brine column, where they are transferred to the salt tank. There, the salts are concentrated before removal through a centrifuge.

The salts in produced water cover a variety of species, but generally are categorized into monovalent salts (typically sodium and potassium), and divalent salts (typically calcium and magnesium). The divalent salts cannot be effectively precipitated in the same manner as the monovalent salts, so a separate calcium removal process may be installed. Effective calcium control is accomplished as the divalent salts are collected, reacted and removed through a centrifuge with the centrate overflow returning to the process.

Current methods of removing the salt crystals from the bottom of the brine column involves a lot of equipment, including but not limited to complicated and expensive centrifugal, centrifuge pump filtration systems, a salt tank, a centrate tank, and a density measurement device. Reducing the footprint of the system required to remove the salt crystals and other contaminants is important for making more efficient use of space, reducing off-shore construction costs, and increasing ease of system operation and maintenance.

SUMMARY OF THE INVENTION

A system for recovering salt from a rich MEG stream being fed into a flash separator, includes a first desanding hydrocyclone located in a recirculation loop of the flash separator; a first solids fluidization device located at a bottom end of a brine column of the flash separator and which includes means for causing a first motive fluid to exit the device in a swirling motion and contact salt components residing in the brine column; and a first removal device located above the solids fluidization device for transporting the salt slurry stream created by the swirling motive fluid away from the brine column to a second desanding hydrocyclone located outside of the flash separator and brine column.

A small portion (preferably less than 10%) of the total recirculation pump flow rate should be introduced into the first desanding hydrocyclone. The overflow of the second desanding hydrocyclone is a source of the first swirling motive fluid stream. The first salt slurry stream can be diluted with a produced water, condensate water, or seawater stream (or some combination thereof) prior to it entering the second desanding hydrocyclone.

An accumulator is arranged to receive the underflow stream of the second desanding hydrocyclone. A shut-off valve, located between the second desanding hydrocyclone and the accumulator, is shut off when the salt level in the accumulator reaches a predetermined height relative to that of the accumulator. Preferably, the predetermined height is about 50% of the height of the accumulator.

The accumulator includes a second fluidization device arranged at the bottom end of the accumulator and which includes means for causing a second motive fluid to exit the fluidization device in a swirling motion and fluidize salt components residing in the brine column. A second removal device transports the salt slurry stream created by the swirling motive fluid away from the accumulator and the salt slurry stream may be discharged overboard. The source of the second swirling motive fluid stream is a produced water stream, a condensate water stream, a seawater stream, or some combination thereof.

A HYDROTRANS™ solids fluidization device (Cameron Process Systems, Houston, Tex.) is suitable for use as the first and second fluidization devices. Any other device may be used as the fluidization device provided the device creates a swirling (e.g., vertiginous, rotating, or cyclonic) motive fluid flow when the flow exits the device.

A method of recovering MEG from a rich-MEG stream includes the steps of:
i. passing a portion of a recirculation loop MEG stream to a first desanding hydrocyclone located within a flash separator;
ii. introducing a first swirling motive fluid stream into a bottom end of a brine column of the flash separator to form a first salt slurry stream; and
iii. passing the first salt slurry stream to a second desanding hydrocyclone located downstream of the flash separator.

The first salt slurry stream can be diluted with at least one of a produced water stream, a condensate water stream, and a seawater stream before it enters the second desanding hydrocyclone. The source of the first swirling motive fluid stream is an overflow stream of the second desanding hydrocyclone.

The method can also include the steps of:
iv. passing an underflow stream from the second desanding hydrocyclone to an accumulator; and
v. introducing, after step iv, a second swirling motive fluid stream into a bottom end of the accumulator to form a second salt slurry stream.

The source of the second swirling motive fluid stream is a produced water stream, a condensate stream, a salt water stream, or some combination thereof. A valve, located between the second desanding hydrocyclone and the accumulator, is shut when the salt level within the accumulator is at a predetermined height of the accumulator (e.g. at about 50% of the height of the accumulator).

The objectives of this invention are to (1) eliminate the need for complicated and expensive centrifugal filters to remove salt; (2) eliminate the need for centrifuge filtration, a salt tank, a centrate tank, and density measurement devices; and (3) require less foot print than the prior art systems and methods and have lower construction costs and be easier to operate and maintain than those prior art systems and methods.

ELEMENTS AND NUMBERING USED IN THE DRAWINGS

Figure 1:
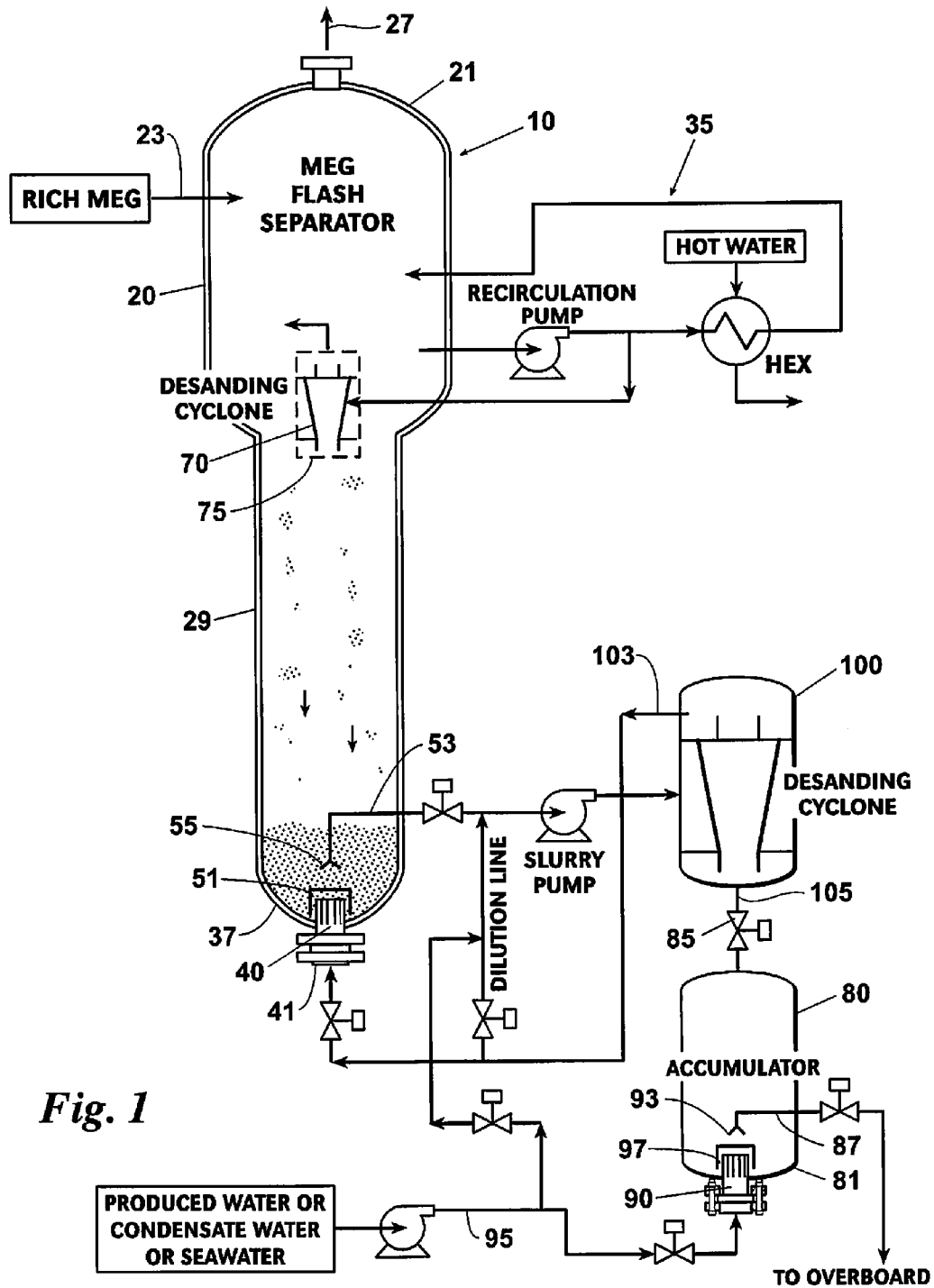
FIG. 1 is a schematic of a preferred embodiment of the MEG recovery system and process. The system includes two desanding hydrocyclones and two solids fluidization devices.
Figure 3:
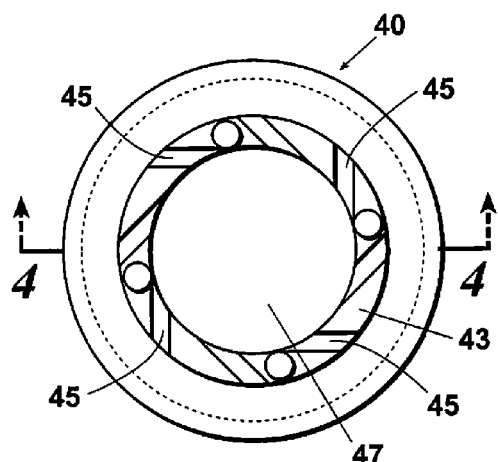
FIG. 3 is top view of the solids fluidization device of FIG. 2.
Figure 5:
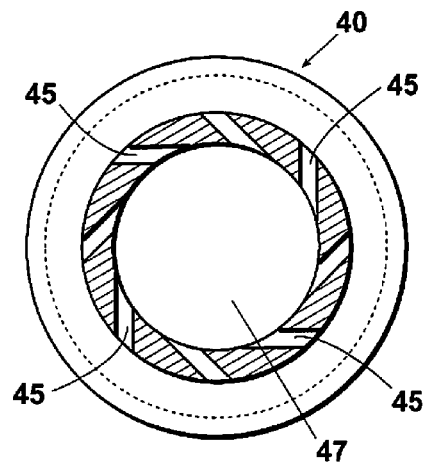
FIG. 5 is a cross-section view of the solids fluidization device of FIG. 2 taken along section line 5-5 of FIG. 2.
Figure 2:
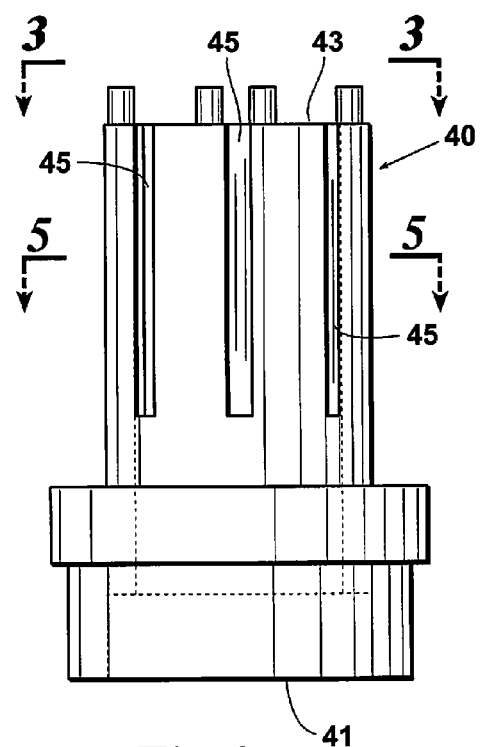
FIG. 2 is a front elevation view of a preferred embodiment of the solids fluidization device of FIG. 1.
Figure 4:
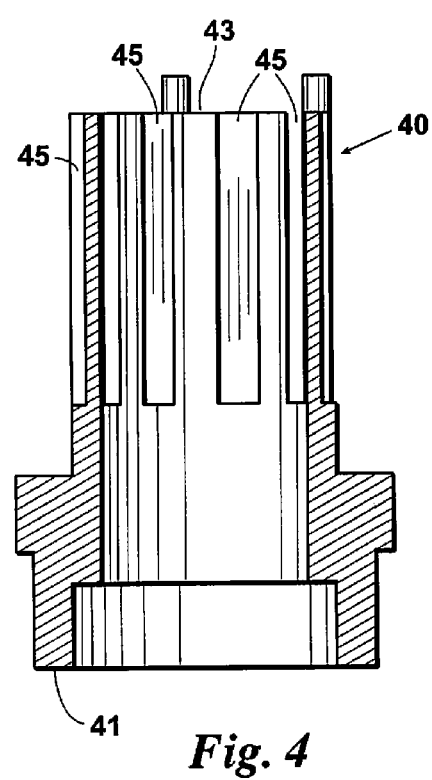
FIG. 4 is a cross-section view of the solids fluidization device of FIG. 2.

10 MEG recovery system
20 Flash separator
21 Upper end
23 Rich (wet) MEG stream
27 Water and MEG vapor stream
29 Brine or downcomer column or section
35 Hot MEG recycle stream or recycle (recirculation) loop
37 Bottom end
40 First solids fluidization device
41 Inlet or lower inlet end
43 Upper end of 40
45 Slots of 40
47 Central or inner bore
51 First swirling motive fluid stream
53 First salt slurry (discharge) stream
55 First removal device
70 First desanding hydrocyclone
75 Underflow end or stream
80 Accumulator
81 Bottom end
85 Valve
87 Second salt slurry (discharge) stream
90 Second solids fluidization device
93 Second removal device
95 Produced water, condensate water. or seawater (carrier or motive fluid) stream
97 Second swirling motive fluid stream
100 Second desanding hydrocyclone
103 Overflow end or stream
105 Underflow end or stream

DETAILED DESCRIPTION OF THE PREFERRED EMBODIMENTS

Figure 6:
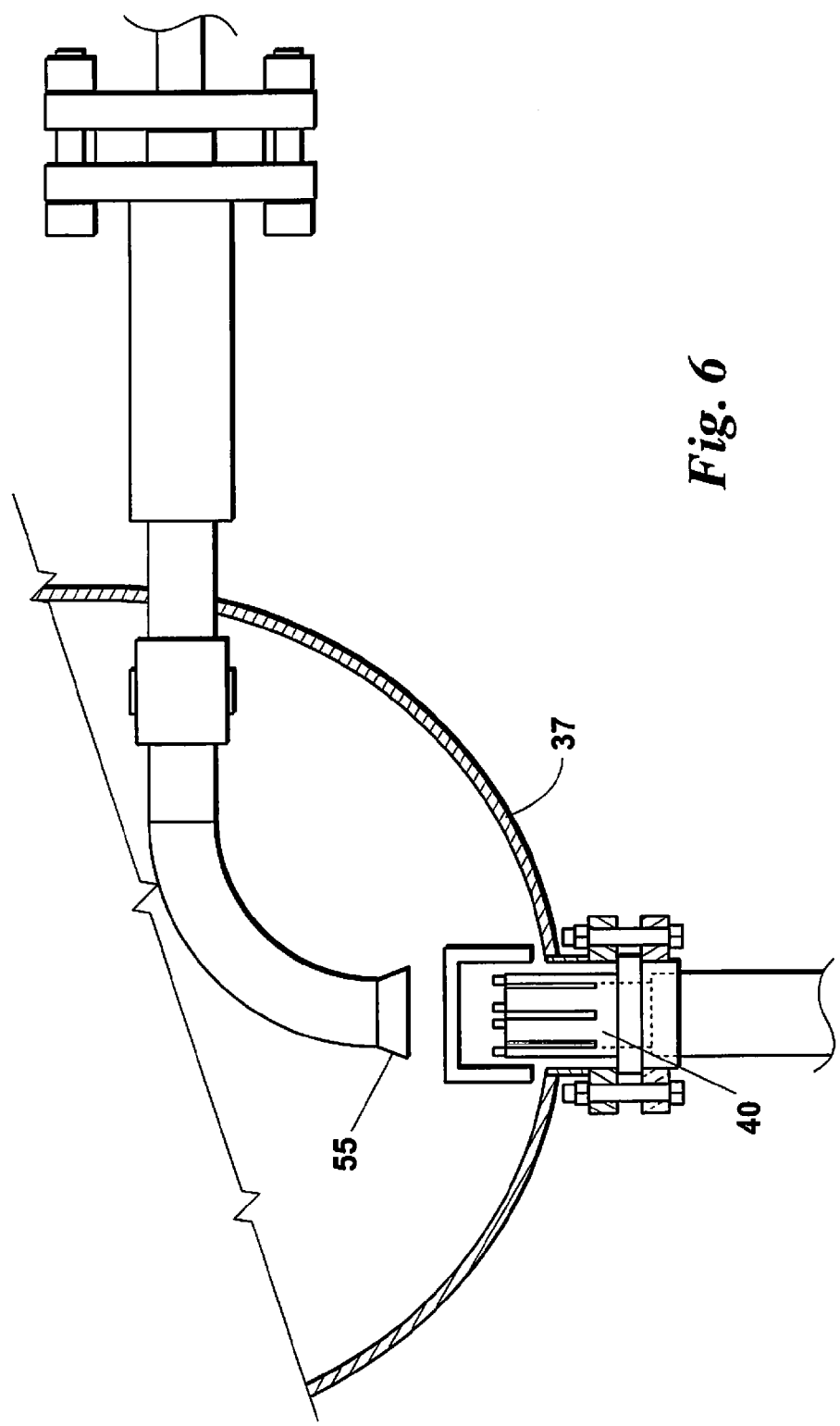
FIG. 6 is an enlarged view of the solids fluidization devices of FIG. 1 and the removal device located directly above each of the solids fluidization devices.

Referring first to FIGS. 1 and 6, a preferred embodiment of a MEG recovery system 10 for a MEG process includes (1) a flash separator 20 having a desanding hydrocyclone 70 located in the hot MEG recycle stream or loop 35 of the separator 20; (2) a solids fluidization device 40 located at the bottom end 37 of the brine column 29; (3) a second desanding hydrocyclone 100 arranged to receive a first salt slurry stream 53 exiting the brine column 29; and (4) an accumulator 80 arranged to receive an underflow stream 105 of the second desanding hydrocyclone 100 and having a second solids fluidization device 90 for producing a second salt slurry stream 87.

Flash separator 20 is of a kind well known in the art. In the separator 20 a rich (wet) MEG inlet stream 23 is brought into contact with a hot MEG recycle loop 35. The MEG and water components of the rich MEG stream 23 are flashed and exit the upper end 21 of the separator 20 as a water and MEG vapor stream 27. The salt components 27 of the rich MEG inlet stream 23 precipitate in the brine column 29 of the separator 20. A MEG/brine transition zone (not shown) can form in the column between the MEG and the brine, but the desanding hydrocyclone 70 facilitates the settling of salt into the brine column 29 and, therefore, helps prevent salt from rising up in the column and negatively affecting the performance of the separator 20.

The desanding hydrocyclone 70 of flash separator 20 reduces the salt concentration in the heat exchanger of the recycle loop 35 by removing salt particles in the stream diverted from the loop 35 and introduced to the desanding hydrocyclone 70. A small portion (preferably less than 10%) of the total recirculation pump flow rate should be introduced into the desanding hydrocyclone 70. The underflow stream 75 from the desanding hydrocyclone 70 enters the brine or downcomer column 29 of the flash separator 20. A MOZLEY® desanding hydrocyclone (Cameron Process Systems, Houston, Tex.) is a suitable desanding hydrocyclone 70.

Solids fluidization device 40 is arranged at the bottom end 37 of the column 29. The device 40 includes means which produce or cause a swirling (e.g. vertiginous, rotary or cyclonic) motion or flow 51 of the motive fluid as it exits device 40. One suitable device 40 is a HYDROTRANS™ solids fluidization and removal device (Cameron Process Systems, Houston, Tex.). Any other device may be used as the fluidization device provided the device creates a swirling (e.g., vertiginous, rotating, or cyclonic) motive fluid flow when the flow exits the device.

Referring to FIGS. 2-5, the HYDROTRANS™ device includes a plurality of spaced-apart slots 45 arranged tangential to, surrounding, and in communication with an inner bore 47 which receives a motive fluid stream 103 at the lower inlet end 41 of the device. Motive fluid steam 103—which comes from the overflow end of the second desanding hydrocyclone 100—exits the slots 45 of device 40 as a swirling motive fluid stream 51. The swirling motion of the motive fluid stream 51 mixes with the solid/salt already residing in the bottom of column 29 to fluidize the salt, thereby creating a salt slurry stream 53.

Unlike the desanding hydrocyclones 70, 100—which produce a cyclonic flow within the device but a straight over- and underflow exiting the device (i.e., straight in, cyclonic within, and straight out)—the solids fluidization device 40 (and 90) produces this type of flow external to the device (i.e., straight in and rotary or cyclonic out).

A removal device 55, which can be a slurry discharge head, resides just above the upper end 43 of solids fluidization device 40. Removal device 55 carries the salt slurry stream 53 to the second desanding hydrocyclone 100. Prior to entering the second desanding hydrocyclone, the salt slurry stream 53 can be diluted with a produced water, condensate water, or seawater stream 95 (or some combination thereof). The solids separated in the hydrocyclone 100 exit as an underflow stream 105 and are passed to an accumulator 80; the overflow stream 103 is passed back to solids fluidization device 40. When the salt level in the accumulator 80 reaches a predetermined height, preferably about 50% of the accumulator's height, the valve 85 located between the desanding hydrocyclone 100 and the accumulator 80 should be closed.

Removing the salt from the accumulator 80 occurs in the same manner as does removing the salt from the brine column 29. A solids fluidization device 90, the same or similar to that of solids fluidization device 40, is arranged at the bottom end 81 of the accumulator 80. A produced water, condensate water, or seawater stream 95 (or some combination thereof) enters the device 90 and is converted into a swirling motive fluid stream 97 which fluidizes the salt components residing in the accumulator 80 and creates a salt slurry 87.

A removal device 93, which can be a slurry discharge head, resides just above solids fluidization device 90. Removal device 93 carries the salt slurry stream 87 away from the accumulator 80, where it can be discharged overboard.

A method of removing salt from a rich MEG stream which makes use of system 10 includes the steps of:
 i. passing a portion of the hot MEG stream in the recycle or recirculation loop 35 of the flash separator 20 to a desanding hydrocyclone 70 located in the recycle or recirculation loop 35;
 ii. introducing a swirling motive fluid stream 51 into the bottom end 37 of the brine column to form a first salt slurry stream 53;
 iii. pumping the first salt slurry stream 53 to a second desanding hydrocyclone 100
 iv. closing a valve 85 located between the desanding hydrocyclone 100 and the accumulator 80;
 v. introducing a swirling motive fluid stream 97 into the bottom end 81 of the accumulator 80 to form a second salt slurry (discharge) stream 87.

A small portion (preferably less than 10%) of the total recirculation pump flow rate should be introduced into the desanding hydrocyclone 70 in step i. The valve 85 should be closed when the salt level is at about 50% of the accumulator height.

The method may also include the step of diluting the first salt slurry stream 53 with a produced water, condensate water, or seawater stream 99 prior to it entering the second desanding hydrocyclone 100 to prevent plugging by high solid concentration. An overflow stream 103 from the second desanding hydrocyclone 100 may be used as the source for the swirling motive fluid stream 51. A produced water, condensate water, or salt water stream 95 can be used as the source for swirling motive fluid stream 97. The swirling motive fluid streams 51, 97 are preferably produced by solids fluidization devices 40, 90, respectively, or any device that produces a swirling motive fluid flow upon the flow exiting the device.

Salt removal system 10 and the method for its use is an improvement over prior art systems and methods. The prior art makes use of complicated and expensive centrifugal filters to remove salt, along with centrifuge filtration, a salt tank, a centrate tank, and density measurement devices, none of which are required by system 10 and the method for its use. System 10 also requires less foot print than the prior art systems and methods, has lower construction costs, and is easier to operate and maintain than those prior art systems.

While preferred embodiments of system 10 and a method for its use have been described in detail, the scope of the invention is defined by the following claims.

What is claimed:

1. A system for removing salt from a rich MEG stream being fed into a flash separator, the system comprising:
 a first desanding hydrocyclone located in a recirculation loop of the flash separator and arranged so an underflow of the first desanding hydrocyclone is introduced into a brine column of the flash separator;
 a first solids fluidization device arranged at a lower end of the brine column and in communication with a first motive fluid stream, the first solids fluidization device including means for causing the first motive fluid stream to swirl when exiting the first fluidization device; and
 a first removal device located above the first solids fluidization device and arranged to carry a first salt slurry stream created by the swirling motive fluid away from the brine column to a second desanding hydrocyclone located outside of the brine column.

2. A system according to claim 1 further comprising an accumulator arranged to receive an underflow stream of the second desanding hydrocyclone.

3. A system according to claim 2 further comprising a shut-off valve located between the second desanding hydrocyclone and the accumulator.

4. A system according to claim 2 further comprising the accumulator including a second solids fluidization device arranged at a lower end of the accumulator in communication with a second motive fluid stream, the second solids fluidization device including means for causing the second motive fluid stream to swirl when exiting the second fluidization device.

5. A system according to claim 4 wherein the causing means is a plurality of spaced-apart vertical slots arranged tangential to and surrounding a central bore of the second fluidization device.

6. A system according to claim 4 wherein a source of the second motive fluid stream is at least one of a produced water, condensate water, or seawater stream.

7. A system according to claim 1 wherein an overflow of the second desanding hydrocyclone is a source of the first motive fluid stream.

8. A system according to claim 1 wherein first salt slurry stream is diluted with at least one of a produced water, condensate water, or seawater stream.

9. A system according to claim 1 wherein the causing means of the first fluidization means is a device having a plurality of spaced-apart vertical slots arranged tangential to and surrounding a central bore of the first fluidization device.

10. A method of removing salt from a rich-MEG stream, the method comprising the steps of:
 i. passing a portion of a recirculation loop MEG stream to a first desanding hydrocyclone located within a flash separator;
 ii. introducing a first swirling motive fluid stream into a bottom end of a brine column of the flash separator to form a first salt slurry stream; and
 iii. passing the first salt slurry stream to a second desanding hydrocyclone located outside of the flash separator.

11. A method according to claim 10 wherein a source of the first swirling motive fluid stream is an overflow stream of the second desanding hydrocyclone.

12. A method according to claim 10 further comprising the step of diluting the first salt slurry stream with at least one of a produced water stream, a condensate water stream, and a seawater stream prior to it entering the second desanding hydrocyclone.

13. A method according to claim 10 further comprising the steps of:

passing an underflow stream from the second desanding hydrocyclone to an accumulator; and introducing a second swirling motive fluid stream into a bottom end of the accumulator to form a second salt slurry stream.

14. A method according to claim 13 further comprising the step of closing a valve located between the second desanding hydrocyclone and the accumulator when a salt level within the accumulator is at a predetermined height of the accumulator.

15. A method according to claim 11 wherein a source of the second swirling motive fluid stream is at least one of a produced water stream, a condensate stream, and a salt water stream.

* * * * *